United States Patent [19]
Aoki et al.

[11] 4,092,411
[45] May 30, 1978

[54] ANTIBACTERIAL COMPOSITION

[75] Inventors: Hatsuo Aoki, Ikeda; Toyozi Nishiura, Toyonaka; Hiroshi Imanaka, Osaka, all of Japan

[73] Assignee: Fujisawa Pharmaceutical Co., Ltd., Osaka, Japan

[21] Appl. No.: 806,147

[22] Filed: Jun. 13, 1977

[30] Foreign Application Priority Data

Jun. 18, 1976  Japan .................................. 51-72458

[51] Int. Cl.² ............................................. A61K 35/00
[52] U.S. Cl. .................................................. 424/114
[58] Field of Search ........................ 424/272, 244, 114

[56] References Cited

U.S. PATENT DOCUMENTS 3,923,977  12/1975  Aoki et al. ........................... 424/118

OTHER PUBLICATIONS

The Merck Index, 8th Ed., 1968, Merck & Co., Inc., Rahway, N.J., pp. 314 and 315.

Primary Examiner—Jerome D. Goldberg
Attorney, Agent, or Firm—Dayton R. Stemple, Jr.

[57] ABSTRACT

Antibacterial synergistic mixture of Nocardicin A and cycloserine or their respective pharmaceutically acceptable salts.

3 Claims, No Drawings

ANTIBACTERIAL COMPOSITION

BACKGROUND OF THE INVENTION

The present invention relates to an antibacterial composition. More particularly, it relates to an antibacterial composition comprising Nocardicin A or its salt and cycloserine or its salt.

Nocardicin A is known as a valuable antibiotic having antibacterial activities against Gram-positive bacteria and Gram-negative bacteria, especially pathogenic Pseudomonas species, and is disclosed under the code name of the antibiotic FR-1923 substance in literatures, e.g. U.S. Pat. No. 3,923,977 and German Offenlegungsschrift No. 2,242,699, in which said antibiotic is defined by the various physico-chemical properties without the chemical structure thereof, but, as a result of further investigation, its chemical structure has been identified and assigned as follows.

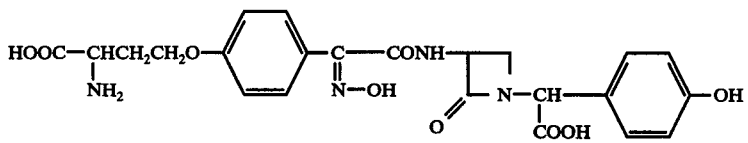

Further, cycloserine is also known as an antibiotic, especially as an antituberculotic agent (vide, e.g. ANTIBIOTICS AND CHEMOTHERAPY Vol. 5, pages 182–205, 1955).

Only for reference to states of the arts, it is noted that said literature (ANTIBIOTICS AND CHEMOTHERAPY Vol. 5, pages 182–205) discloses the synergistic effect of the combination of cycloserine and penicillins, bacitracin, oxytetracycline, chlortetracycline, streptomycin or chloromphenicol against Gram-positive and Gram-negative bacteria. The inventors of the present invention have conducted extensive studies for enhancing the antimicrobial activities of Nocardicin A per se for the therapeutic purpose thereof. As a result of such extensive studies, the inventors of the present invention have finally succeeded in finding that antibacterial activities of Nocardicin A against various Gram-negative bacteria can be remarkably enhanced by combination with cycloserine. That is, the inventors of the present invention have found that Nocardicin A exhibits a synergistic antibacterial activities by combination with cycloserine. On the other hand, it has been noted that antimicrobial activities of Nocardicin A can not be enhanced by combination with the other antibiotics, for example, penicillins, cephalosporins, etc. As explained, enhancement of antimicrobial activities of Nocardicin A by combination with cycloserine and no enhancement thereof by combination with the other antibiotics are new unexpected and surprising findings, and such behaviors of Nocardicin A are due to the unique properties and chemical structure of Nocardicin A.

Accordingly, the antibacterial composition of the present invention is characterized by the synergistic activity against various pathogenic bacteria, especially Gram-negative bacteria such as *Pseudomonas aeruginosa, Proteus vulgaris* and *Escherichia coli.*

DETAILED DESCRIPTION OF THE PREFERRED EMBODIMENTS OF THE INVENTION

The present invention relates to an antibacterial composition. More particularly, it relates to an antibacterial composition comprising Nocardicin A or its salt and cycloserine or its salt.

Accordingly, an object of the present invention is to provide an antibacterial composition comprising Nocardicin A or its salt and cycloserine or its salt.

Another object of the invention is to provide an antibacterial composition having an excellent antibacterial activity and enhanced therapeutic and preventive effects in human beings and animals.

A further object of the invention is to provide an antibacterial composition having stronger antibacterial activities against Gram-negative bacteria, especially Pseudomonas species.

These and other objects of the invention will be apparent from the description hereinafter.

The antibacterial composition of the present invention comprises, as effective ingredients, a combination of Nocardicin A or its salt and cycloserine or its salt.

The salts of Nocardicin A and cycloserine may include physiologically (e.g. pharmaceutically) acceptable salts such as a metal salt (e.g. sodium, potassium, calcium, barium or magnesium salt), ammonium salt, an amine salt (e.g. ethanolamine, triethylamine, procaine, dibenzylamine or dicyclohexylamine salt), a salt with an inorganic acid (e.g. hydrochloric acid or sulfuric acid salt), a salt with an organic acid (e.g. tartaric acid, lactic acid or methanesulfonic acid salt) and a salt with a basic amino acid (e.g. arginine, ornithine or lysine salt).

The antibacterial composition of the present invention is useful for treating and preventing diseases induced by pathogenic bacteria in human beings and other animals such as poultry, domestic animals, pet animals and experimental animals (e.g. chicken, turkey, duck, quail, cow, cattle, horse, pig, hog, dog, sheep, goat, mink, canary, macaw, mouse, rat or rabbit).

The combination ratio of Nocardicin A or its salt and cycloserine or its salt in the present antibacterial composition may vary depending on the kinds of pathogen and the symptoms of the patients to which the present composition is applied, but may usually be selected within a range of 10:1 to 1:10 by weight, preferably 1:2 to 2:1 by weight, most preferably 1:1.

Further, it is to be noted that the present antibacterial composition may be applied to human beings and other animals in conventional forms, examples of which are illustrated as follows.

For applying to human, it is preferably applied to in the form of intravenous or intramuscular injection. It may also be applied locally in the form of a powder, a suppository or an ointment. When used as an injection, it may be used in admixture with a solid or liquid carrier or diluent which is usually used for the conventional antibiotic injections, and further, may also be used together with other medicines such as analgesics (e.g. lidocaine) which are usually used in injections. The most preferred carrier or diluent is water. When used as a suppository and an ointment, it may be used in admixture with conventional suppository and ointment bases, respectively.

For applying to other animals, it is preferably applied in the form of injection, and for treating mastitis in cow or other animals, it is preferably applied in the form of infusion. It may also be applied locally in a form of a powder or an ointment. When used as an injection or infusion, it may be used in admixture with a solid or liquid carrier or diluent which is usually used for the conventional antibiotic injections or infusions. The most preferred carrier or diluent is water, vegetable oils, paraffins or the like. When used as an ointment, it may be used in admixture with conventional ointment bases.

The dosage of the present antibacterial composition may vary depending on various factors such as weight and age of the patient, the kinds and severity of the infection, and the kinds of the application mode. However, it is to be understood that the optimum dosage of the effective ingredient (i.e. a mixture of Nocardicin A or its salt and cycloserine or its salt) to the patients may be usually selected from the range of 5 to 200 mg/kg/day. More particularly, for instance, in the injection to human being, it may be administered in a dose of about 1 to 5 g/day in adults and in a dose of about 10 to 30 mg/kg/day in children, but not limited thereto. For treating bovine mastitis during lactation drying period, it may be administered in a dose of about 50-500 mg/quarter.

The antibacterial composition as explained above as a strong antibacterial activity against pathogenic Gram-negative bacteria such as *Pseudomonas aeruginosa*, *Proteus vulgaris* and *Escherichia coli*. Especially, it is to be noted that the antimicrobial composition shows a specific and strong synergistic antibacterial activity against pathogenic Pseudomonas species (e.g. *Pseudomonas aeruginosa*) and that the literature (ANTIBIOTICS AND CHEMOTHERAPY) does not teach synergistic effect of cycloserine and Nocardicin A. Accordingly, the present antibacterial composition is useful as a therapeutic agent for infectious diseases by pathogenic bacteria, especially pathogenic Pseudomonas.

And further, it is to be noted that the composition of the present invention shows low toxicity. The toxicity test is shown in the following.

ACUTE TOXICITY TEST

An aqueous solution (0.5 ml.) containing a mixture of monosodium salt of Nocardicin A and cycloserine (1:1 by weight) was intravenously injected into each of three ICR-strain male mice weighing 20 g (Dose 750 mg/kg). The observation was continued for one week after the administration, as the result of which all the tested mice were normal.

The antibacterial activities and the preventing effectiveness against various bacterial infections of the present composition are illustrated by the following experimental tests in vitro and in vivo.

Test 1

Synergistic activity of Nocardicin A and cycloserine against pathogen isolated from patients in the inhibitory concentration in vitro:

On a Nutrient agar containing prescribed amounts of sodium salt of Nocardicin A and cycloserine, was streaked a loopful of overnight-cultured broth of each pathogen (medium: Nutrient broth, a concentration of living organisms: $10^8$ cells/ml.), and incubation was carried out at 37° C for 20 hours and then the growth of the test organisms was observed. The results are shown in the following tables 1-3. In the tables, the symbol "+" means that the test microorganism grew and the symbol "−" means that the test microorganism did not grow.

Table 1

| (*Pseudomonas aeruginosa*, strain 1101-1) | | | | | | | |
|---|---|---|---|---|---|---|---|
| Monosodium salt | | Cycloserine (mcg / ml) | | | | | |
| of Nocardicin A (mcg/ml) | | 0 | 6.3 | 12.5 | 25 | 50 | 100 | 200 |
| | 0 | + | + | + | + | + | + | − |
| | 63 | + | + | + | + | + | − | − |
| | 125 | + | + | + | + | − | − | − |
| | 250 | + | + | + | + | − | − | − |
| | 500 | + | + | − | − | − | − | − |
| | 1000 | + | − | − | − | − | − | − |
| | 2000 | − | − | − | − | − | − | − |

Table 2

| (*Proteus vulgaris*, strain 1431-1) | | | | | | |
|---|---|---|---|---|---|---|
| Monosodium salt | | Cycloserine (mcg / ml) | | | | |
| of Nocardicin A (mcg/ml) | | 0 | 6.3 | 12.5 | 25 | 50 |
| | 0 | + | + | + | + | + |
| | 2 | + | + | + | + | − |
| | 4 | + | + | + | − | − |
| | 8 | + | + | + | − | − |
| | 16 | + | + | − | − | − |
| | 32 | + | − | − | − | − |
| | 63 | + | − | − | − | − |
| | 125 | − | − | − | − | − |

Table 3

| (*Escherichia coli*, strain NIHJ JC-2) | | | | | | |
|---|---|---|---|---|---|---|
| Monosodium salt | | Cycloserine (mcg / ml.) | | | | |
| of Nocardicin A (mcg/ml) | | 0 | 6.3 | 12.5 | 25 | 50 |
| | 0 | + | + | + | + | − |
| | 8 | + | + | + | + | − |
| | 16 | + | + | + | − | − |
| | 32 | + | + | + | − | − |
| | 63 | + | + | − | − | − |
| | 125 | + | − | − | − | − |
| | 250 | − | − | − | − | − |

As made clear from the above results, the combination of monosodium salt of Nocardicin A and cycloserine shows synergistic inhibitory activity against various bacteria.

Test 2

Effects on the experimentally infected mice:

ICR-strain male mice weighing 20 g (8-10 mice per one group) were used. A prescribed amount of the pathogenic bacteria suspended in 2.5% aqueous mucin solution (0.5 ml.) was inoculated intraperitoneally into each mouse. One hour after the inoculation, the antibiotics as mentioned in the following table were administered subcutaneously, and then survival of the test mice was measured one week after the infection. The results are shown in the following tables 4-6.

Table 4

| (*Pseudomonas aeruginosa*, strain 1101-1) (Challenge dose : 1 × $10^6$ living cells/mouse) | | |
|---|---|---|
| Antibiotics | Dosage per mouse | Survival of test mice/test mice |
| Monosodium salt of Nocardicin A + Cycloserine | 0.6 mg  4 mg | 8 / 8 |
| Monosodium salt of Nocardicin A + Cycloserine | 0.6 mg  1 mg | 6 / 8 |
| Monosodium salt of Nocardicin A | 0.6 mg | 0 / 8 |
| Cycloserine | 4 mg  1 mg | 0 / 10  0 / 10 |

Table 4-continued (*Pseudomonas aeruginosa*, strain 1101-1)
(Challenge dose : 1 × 10⁶ living cells/mouse)

| Antibiotics | Dosage per mouse | Survival of test mice/test mice |
|---|---|---|
| None | — | 0 / 10 |

Table 5

(*Proteus vulgaris*, strain 1431 - 1)
(Challenge dose : 1 × 10⁶ living cells / mouse)

| Antibiotics | Dosage per mouse | Survival of test mice/test mice |
|---|---|---|
| Monosodium salt of Nocardicin A | 0.02 mg | |
| + | | 8 / 8 |
| Cycloserine | 4 mg | |
| Monosodium salt of Nocardicin A | 0.02 mg | |
| + | | 5 / 8 |
| Cycloserine | 1 mg | |
| Monosodium salt of Nocardicin A | 0.02 mg | 0 / 8 |
| Cycloserine | 4 mg | 0 / 10 |
| | 1 mg | 0 / 10 |
| None | — | 0 / 10 |

Table 6

(*Escherichia coli*, strain 1341 - 29)
(Challenge dose : 1 × 10⁶ living cells / mouse)

| Antibiotics | Dosage per mouse | Survival of test mice/test mice |
|---|---|---|
| Monosodium salt of Nocardicin A | 1.25 mg | |
| + | | 8 / 8 |

Table 6-continued (*Escherichia coli*, strain 1341 - 29)
(Challenge dose : 1 × 10⁶ living cells / mouse)

| Antibiotics | Dosage per mouse | Survival of test mice/test mice |
|---|---|---|
| Cycloserine | 0.75 mg | |
| Monosodium salt of Nocardicin A | 0.15 mg | |
| + | | 6 / 8 |
| Cycloserine | 0.75 mg | |
| Monosodium salt of Nocardicin A | 1.25 mg | 2 / 8 |
| | 0.15 mg | 0 / 8 |
| Cycloserine | 0.75 mg | 0 / 10 |
| None | — | 0 / 10 |

As made clear from the above results, the synergistic inhibitory activity of monosodium salt of Nocardicin A and cycloserine was also confirmed by in vivo test.

The antibacterial compositions of the present invention are illustrated by the following Examples.

EXAMPLE 1 (Preparation of an injection)

A sterile mixture of monosodium salt of Nocardicin A (250 mg) and cycloserine (250 mg) was inserted into a vial and the vial was sealed. And when using as an injection, distilled water (2 ml.) for injection is added thereto.

What is claimed is:

1. An antibacterial composition comprising Nocardicin A and cycloserine or their pharmaceutically acceptable salts respectively in a ratio of 1:10 to 10:1 by weight.

2. The antibacterial composition according to claim 1 wherein said ratio is 1:2 to 2:1.

3. The antibacterial composition according to claim 1 wherein said ratio is 1 to 1.

* * * * *